(12) United States Patent
Mitteldorf

(10) Patent No.: US 12,165,769 B2
(45) Date of Patent: Dec. 10, 2024

(54) PREDICTIVE AND INTERACTIVE DIAGNOSTIC SYSTEM

(71) Applicant: Malecare, Inc., New York, NY (US)

(72) Inventor: Darryl Mitteldorf, New York, NY (US)

(73) Assignee: Malecare, Inc., New York, NY (US)

( * ) Notice: Subject to any disclaimer, the term of this patent is extended or adjusted under 35 U.S.C. 154(b) by 0 days.

(21) Appl. No.: 17/887,818

(22) Filed: Aug. 15, 2022

(65) Prior Publication Data
US 2023/0044314 A1    Feb. 9, 2023

Related U.S. Application Data

(63) Continuation of application No. 15/662,806, filed on Jul. 28, 2017, now Pat. No. 11,450,432.
(Continued)

(51) Int. Cl.
*G16H 50/20*    (2018.01)
*A61B 5/00*    (2006.01)
(Continued)

(52) U.S. Cl.
CPC .......... *G16H 50/20* (2018.01); *A61B 5/0022* (2013.01); *A61B 5/02055* (2013.01);
(Continued)

(58) Field of Classification Search
CPC ........ G16H 50/20; G16H 15/00; G16H 40/67; A61B 5/0022; A61B 5/02055;
(Continued)

(56) References Cited

U.S. PATENT DOCUMENTS 10,431,342 B2 * 10/2019 Kovatchev .............. G16Z 99/00
10,468,135 B2 * 11/2019 Lynn ........................ H04N 9/87
(Continued)

FOREIGN PATENT DOCUMENTS

WO    WO-2016123481 A2 *    8/2016    .............. C12Q 1/68

OTHER PUBLICATIONS

"A new day in Cancer Care is here welcome to Cancerlife," CancerLife, 1 page, (2014). [Retrieved from the Internet Nov. 12, 2019: <URL: https://web.archive.org/web/20140517053950/https://cancerlife.com/>]. [Author Unknown].
(Continued)

*Primary Examiner* — Eliza A Lam
(74) *Attorney, Agent, or Firm* — Alston & Bird LLP

(57) ABSTRACT

Techniques for providing health monitoring with mobile devices are discussed herein. Some embodiments may include a method including: receiving symptom data via a user interface of a mobile device over time, the symptom data defining symptoms and severities associated with the symptoms for a user; determining, by processing circuitry of the mobile device, time data associated with the symptom data; generating, by the processing circuitry, graph data based on the symptom data and the time data; generating, by the processing circuitry, a graph data report based on the graph data; and providing, by the processing circuitry, the graph data report to one or more servers via a network.

20 Claims, 11 Drawing Sheets

FIG. 3

Related U.S. Application Data

(60) Provisional application No. 62/370,092, filed on Aug. 2, 2016.

(51) Int. Cl.

| | | |
|---|---|---|
| *A61B 5/0205* | (2006.01) | |
| *A61B 5/024* | (2006.01) | |
| *A61B 5/026* | (2006.01) | |
| *A61B 5/0531* | (2021.01) | |
| *A61B 5/0537* | (2021.01) | |
| *A61B 5/11* | (2006.01) | |
| *A61B 5/1455* | (2006.01) | |
| *G06F 3/04842* | (2022.01) | |
| *G06F 3/0488* | (2022.01) | |
| *G06T 11/20* | (2006.01) | |
| *G16H 15/00* | (2018.01) | |
| *G16H 40/67* | (2018.01) | |

(52) U.S. Cl.
CPC ........ *A61B 5/6898* (2013.01); *G06F 3/04842* (2013.01); *G06F 3/0488* (2013.01); *G06T 11/206* (2013.01); *G16H 15/00* (2018.01); *G16H 40/67* (2018.01); *A61B 5/0077* (2013.01); *A61B 5/024* (2013.01); *A61B 5/026* (2013.01); *A61B 5/0531* (2013.01); *A61B 5/0537* (2013.01); *A61B 5/1112* (2013.01); *A61B 5/14551* (2013.01); *A61B 5/7475* (2013.01)

(58) Field of Classification Search
CPC ..... A61B 5/6898; A61B 5/0077; A61B 5/024; A61B 5/026; A61B 5/0531; A61B 5/0537; A61B 5/1112; A61B 5/14551; A61B 5/7475; G06F 3/04842; G06F 3/0488; G06T 11/206
See application file for complete search history.

(56) References Cited

U.S. PATENT DOCUMENTS

| | | |
|---|---|---|
| 11,450,432 B2 | 9/2022 | Mitteldorf |
| 2007/0156032 A1 | 7/2007 | Gordon et al. |
| 2008/0088436 A1 | 4/2008 | Reeves et al. |
| 2012/0166218 A1* | 6/2012 | Reiner ............... G06Q 30/0278 705/2 |
| 2014/0316793 A1 | 10/2014 | Pruit |
| 2015/0313529 A1* | 11/2015 | Nevo ................... A61B 5/4809 600/595 |
| 2016/0253480 A1 | 9/2016 | Comish |
| 2016/0350509 A1* | 12/2016 | Sharma .............. A61B 5/02055 |
| 2017/0080346 A1 | 3/2017 | Abbas |
| 2017/0083680 A1* | 3/2017 | Adolphus ............... H04W 4/21 |
| 2017/0124292 A1 | 5/2017 | Shafer et al. |

OTHER PUBLICATIONS

"Your mobile companion that takes charge of your cancer care needs at home, so you can focus on life.," Medocity, Inc., 6 pages, (2015). [Retrieved from the Internet Nov. 12, 2019: <URL: https://web.archive.org/web/20150828055122/http://icancerhealth.com/ >]. [Author Unknown].

"iCancerHealth Platform from Medocity + on Vimeo," Vimeo, Inc., 2 pages, (2014). [Retrieved from the Internet Nov. 12, 2019: <URL: https://vimeo.com/116205479>]. [Author Unknown].

"Brochure: 360° virtual care at home," Medocity, Inc., 2 pages, (2014). [Retrieved from the Internet Nov. 12, 2019: <URL: https://web.archive.org/web/20150828055122/http://icancerhealth.com/>]. [Author Unknown].

U.S. Appl. No. 15/662,806 Non-Final Office Action mailed Aug. 8, 2019.

U.S. Appl. No. 15/662,806 Final Office Action mailed Apr. 17, 2020.

U.S. Appl. No. 15/662,806 Non-Final Office Action mailed Nov. 30, 2020.

U.S. Appl. No. 15/662,806 Final Office Action mailed Jun. 21, 2021.

U.S. Appl. No. 15/662,806 Advisory Action mailed Aug. 30, 2021.

U.S. Appl. No. 15/662,806 Non-Final Office Action mailed Dec. 9, 2021.

U.S. Appl. No. 15/662,806 Notice of Allowance mailed Jun. 10, 2022.

U.S. Appl. No. 15/662,806 Amended Notice of Allowance mailed Aug. 13, 2022.

Jenkin, "Chernoby's tomb," The Lancet Oncology, vol. 18, Issue 6, p. 718, (Jun. 2017).

\* cited by examiner

PREDICTIVE AND INTERACTIVE DIAGNOSTIC SYSTEM

CROSS-REFERENCE TO RELATED APPLICATIONS

The present application is a continuation of U.S. application Ser. No. 15/662,806, titled "PREDICTIVE AND INTERACTIVE DIAGNOSTIC SYSTEM," filed Jul. 28, 2017, which claims priority to U.S. Provisional Application Ser. No. 62/370,092, titled "MOBILE DEVICE HEALTH MONITORING, filed Aug. 2, 2016, the contents of which are incorporated herein by reference in their entirety.

FIELD

Embodiments of the disclosure relate, generally, to techniques for providing predictive and interactive diagnostics, and more particularly to mobile device health monitoring.

BACKGROUND

Physicians ask patients to recall when and where they experience a symptom or side effect, such as a hot flash, pain, nausea, anxiety, odd skin sensations, etc. The symptoms or side effects may be provided to diagnostic systems to facilitate patient treatment. A diagnostics system may be as simple as an in-person doctor visit, or a technological system. However, patients are often unable to recall symptoms and side effects with any rigor or reliability. In this regard and others as discussed herein, areas for improving current techniques have been identified. Through applied effort, ingenuity, and innovation, solutions to improve such systems have been realized and are described herein.

BRIEF SUMMARY

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Figure 1:
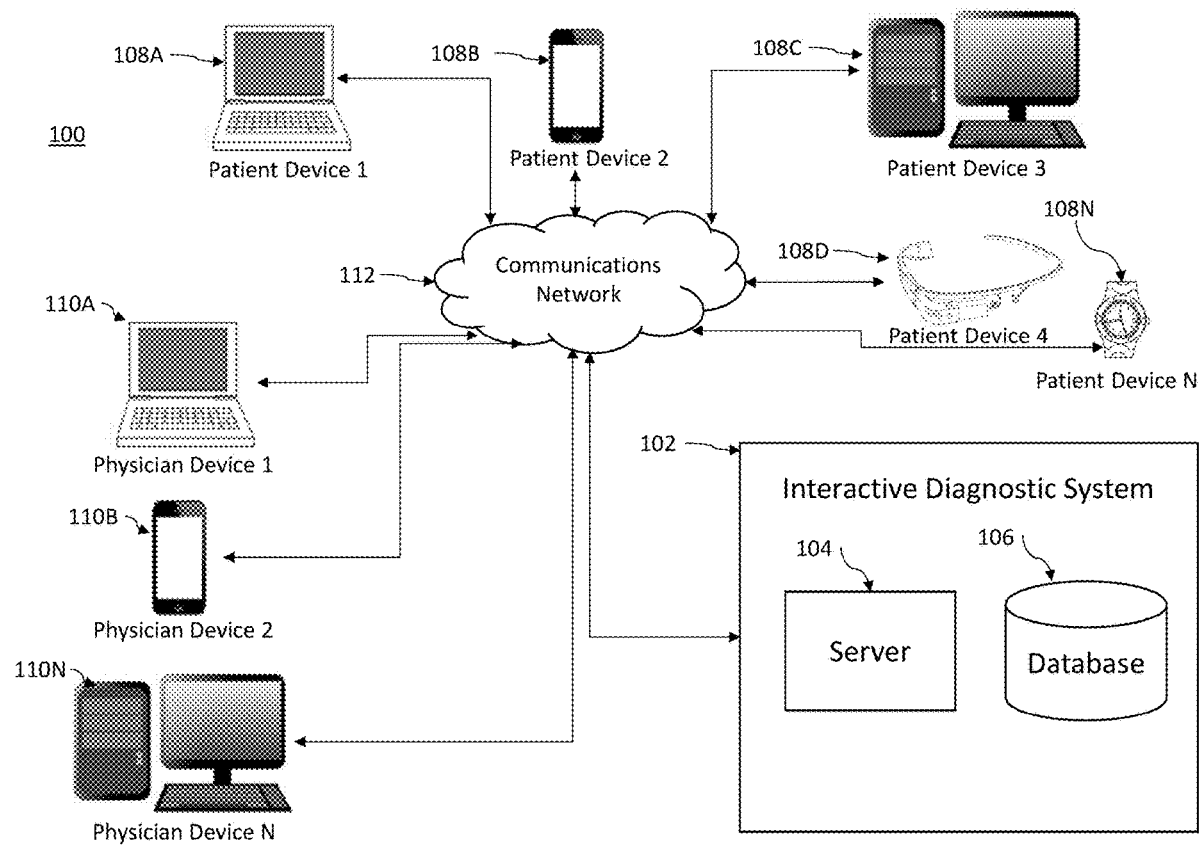
Figure 2:
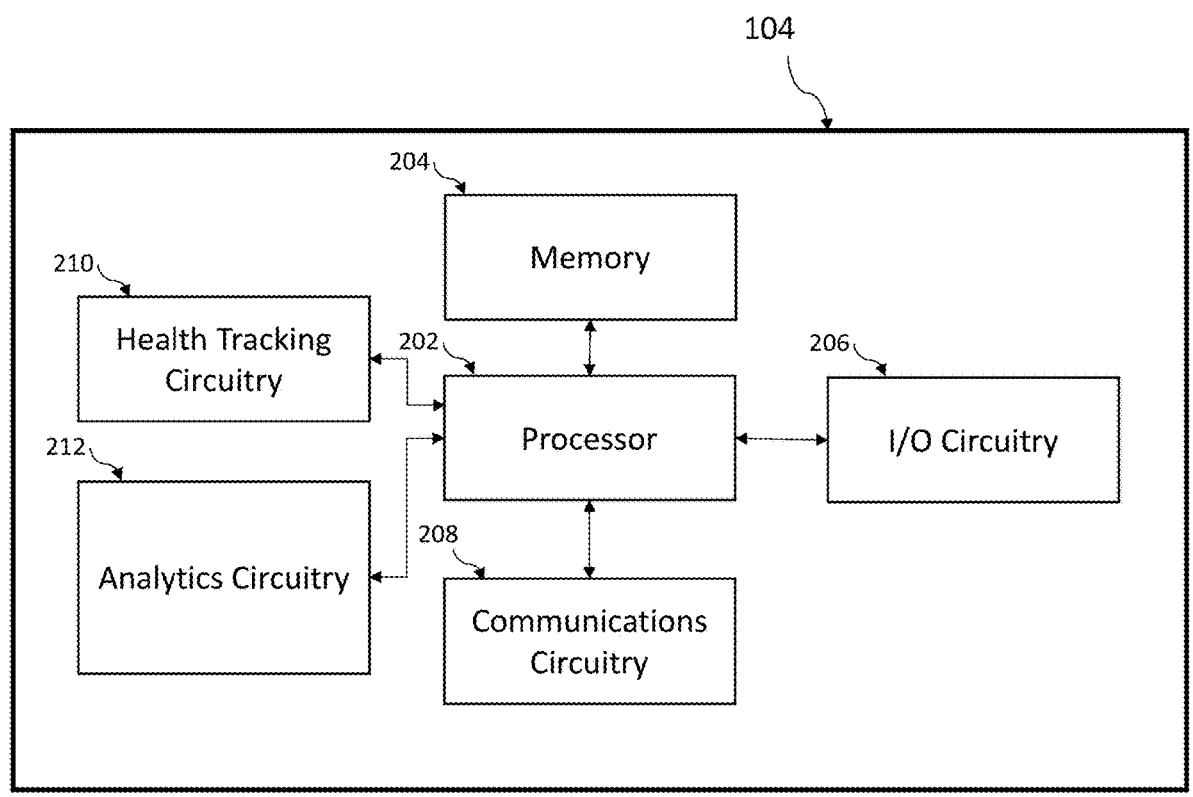
Figure 3:
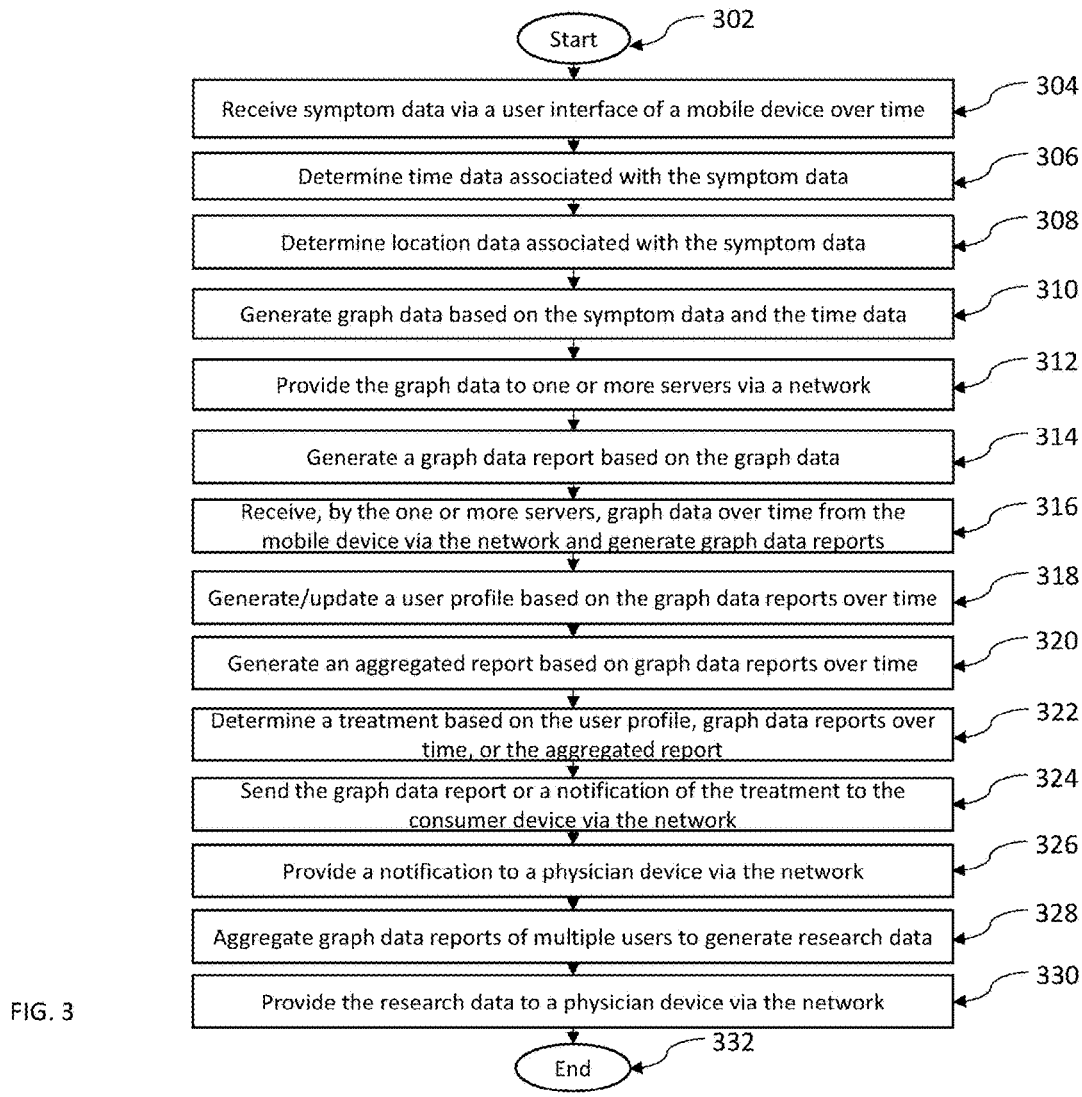
Figure 4:
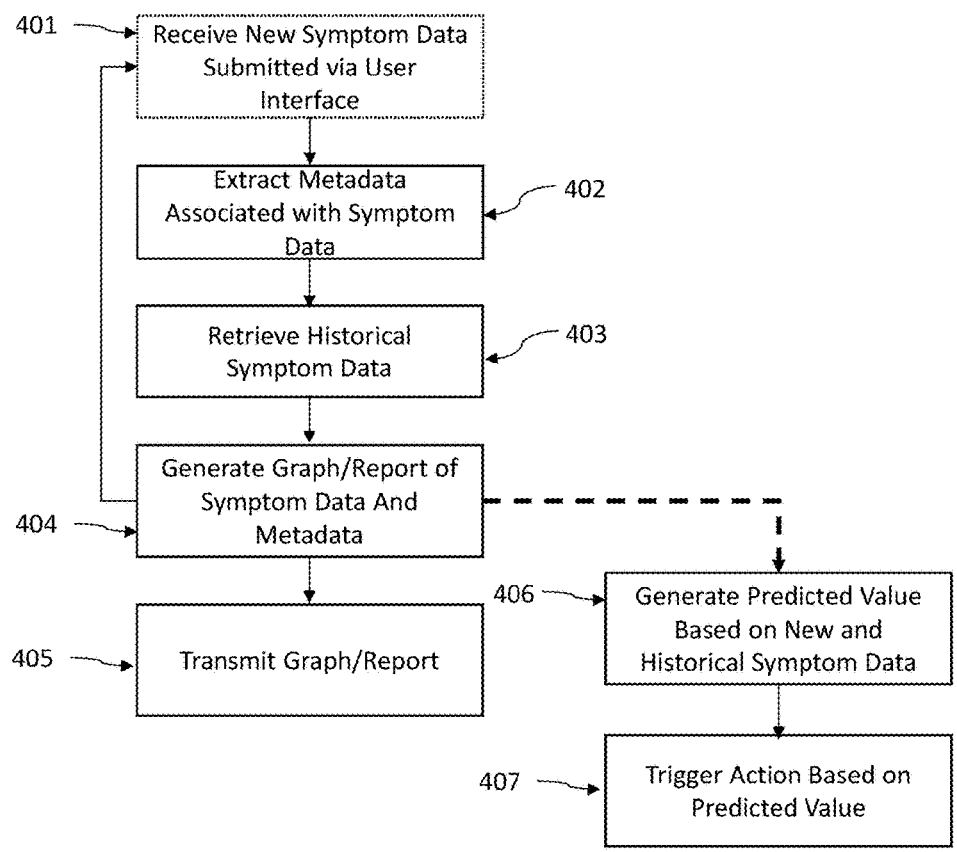
Figure 5:
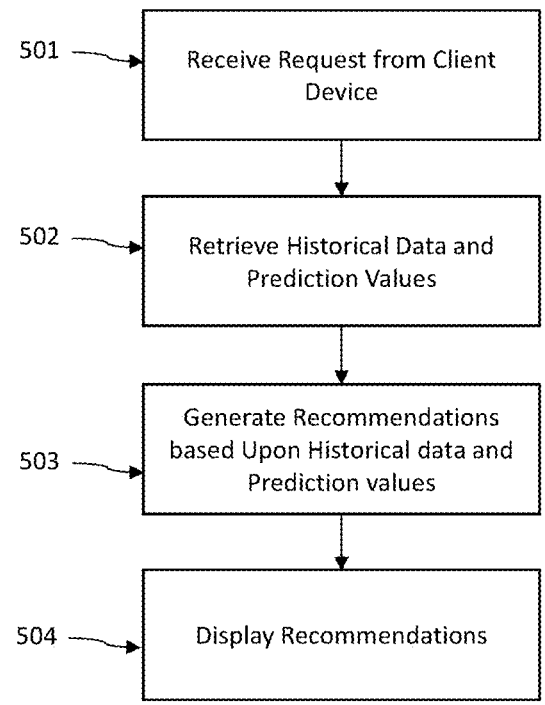
Figure 6:
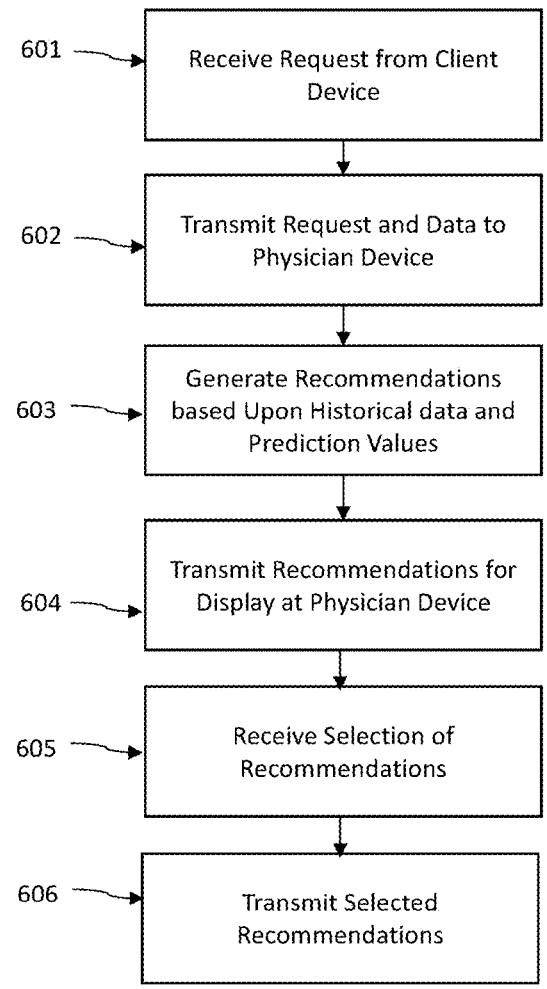
Figure 7:
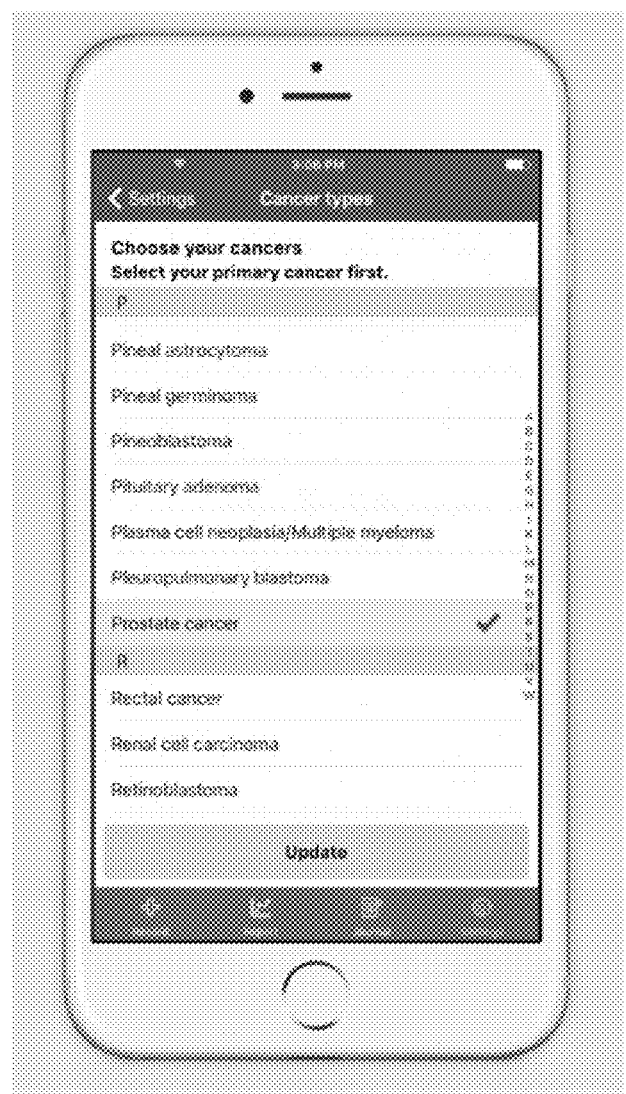
Figure 8:
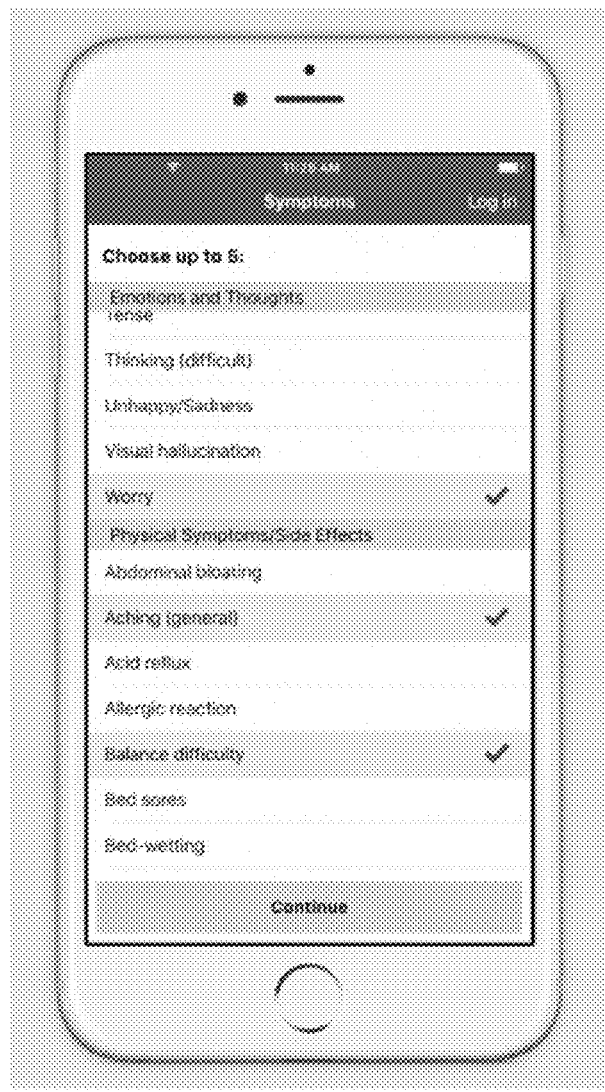
Figure 9:
Figure 9:
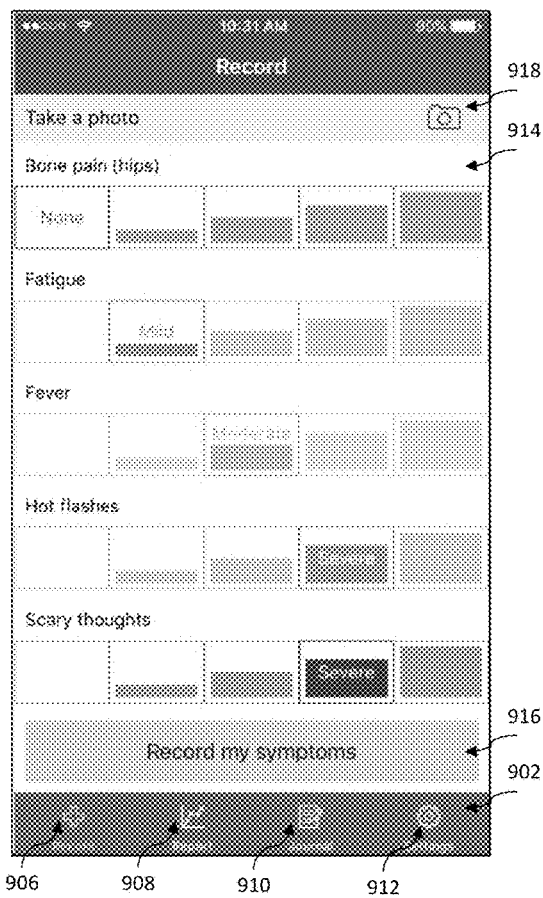
Figure 10:
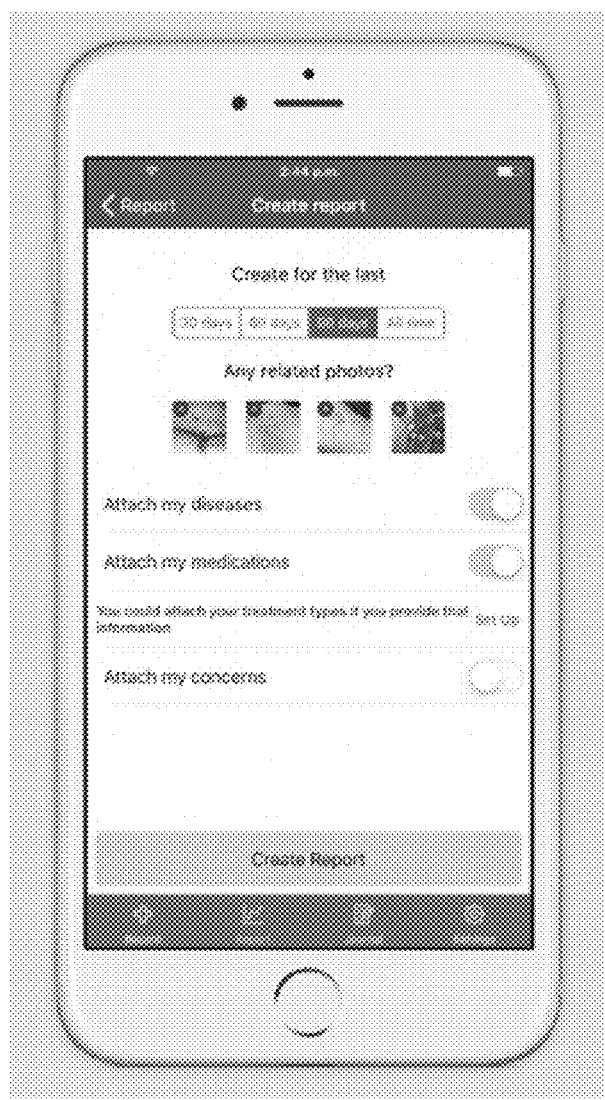
Figure 11:
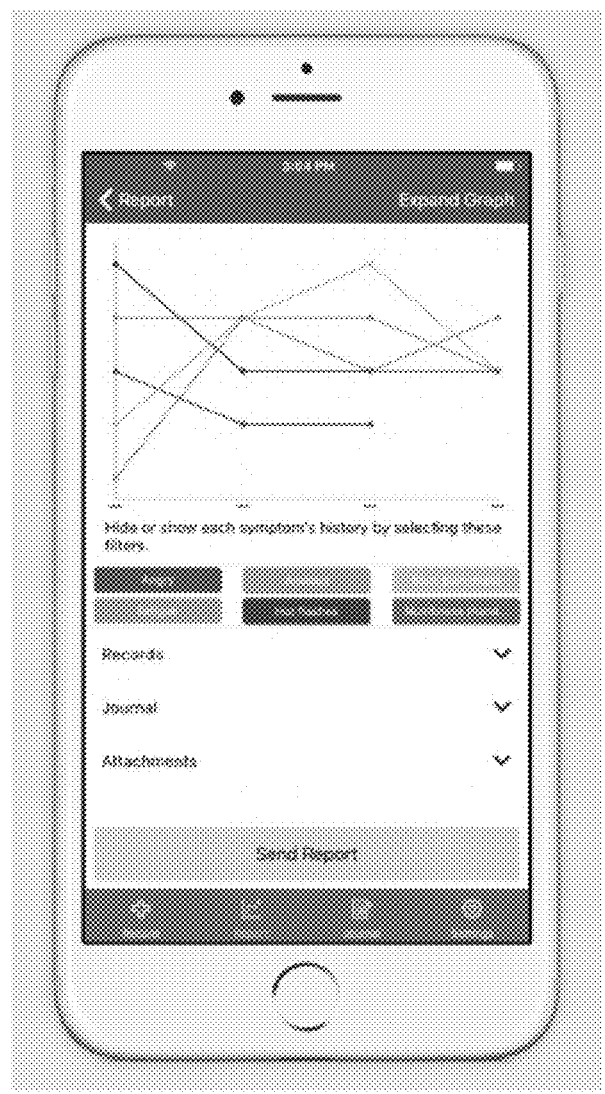

Having thus described some embodiments in general terms, reference will now be made to the accompanying drawings, which are not necessarily drawn to scale, and wherein:

FIG. 1 is an exemplary system architecture diagram of a predictive and interactive diagnostic system configured to practice embodiments of the present disclosure;

FIG. 2 is an exemplary schematic diagram of a computing entity according to one embodiment of the present disclosure;

FIG. 3 is an exemplary predictive and interactive diagnostic data flow according to one embodiment of the present disclosure;

FIG. 4 is an exemplary predictive and interactive diagnostic data flow according to one embodiment of the present disclosure;

FIG. 5 is an exemplary predictive and interactive diagnostic data flow according to one embodiment of the present disclosure;

FIG. 6 is an exemplary predictive and interactive diagnostic data flow according to one embodiment of the present disclosure;

FIG. 7 illustrates an exemplary user interface for use with embodiments of the present disclosure;

FIG. 8 illustrates an exemplary user interface for use with embodiments of the present disclosure;

FIG. 9 illustrates an exemplary user interface for use with embodiments of the present disclosure;

FIG. 10 illustrates an exemplary user interface for use with embodiments of the present disclosure; and FIG. 11 illustrates an exemplary user interface for use with embodiments of the present disclosure.

DETAILED DESCRIPTION

Various embodiments of the present disclosure now will be described more fully hereinafter with reference to the accompanying drawings, in which some, but not all embodiments of the disclosure are shown. Indeed, the disclosure may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout.

OVERVIEW

Various embodiments of the disclosure generally relate to an interactive and predictive diagnostic system that utilizes mobile computing devices for the monitoring of patient health, treatment, and the like, in the context of cancer patients. Embodiments of the present disclosure enable cancer patients utilizing mobile client devices to select symptoms, severities, and more as they occur. Embodiments of the present disclosure enable storage and analysis of such symptom and severity data such that the cancer patient may physically display the stored data to a physician in a future appointment. The analyzed data can also be shared via electronic mail or other electronic communication medium. Embodiments of the present disclosure also enable the linkage of uploaded audio, video, and image files with symptom data such that reports are further enhanced along with information about the cancer diagnosis, co-morbidities, medications, treatment types, and concerns.

In some embodiments, the analyzed data is converted to a visual representation, for example a graph, which provides a reduction in time that a doctor might take to understand a patient's side effect and/or symptom progression over time.

Embodiments of the present disclosure also enable cancer patients to elect to receive electronic communications about relevant clinical trials based on their disease type and status, or to share their collected data in an anonymous form for research purposes.

Cancer is a complex disease with complex symptoms and side-effects experienced by patients during their treatment courses. Accurately recalling and conveying the specifics of their experiences to health-care providers during time-limited medical appointments is a challenging—and at times overwhelming—task for patients. The brain of a cancer patient undergoing treatment is often clouded by medication and more. Such inability to recall and convey symptoms and side-effects results in missed opportunities to personalize cancer treatments to the unique variety of a patient's symptoms.

Patients who apply to participate in clinical trials are not always accepted, perhaps because they do not fit the exact requirements needed by the study. Applying and getting rejected can lead to a lack of motivation to attempt to participate in studies, leading to low participation and less fruitful studies due to not enough sample data.

Patients in remote areas or developing countries are sometimes limited in their access to healthcare, leading to poor health. While patients in these remote areas typically always have mobile computing devices and connectivity with a communications network, they typically will not have regular access to a healthcare professional to ask simple or complex questions.

The inventor has identified that contextual diagnoses and tracking of physiological parameters and physical symptoms for cancer patients is not realistic without the use of computing resources. The inventor has also identified that the system resources and time allocated to gathering a statistically significant amount of data in a clinical trial are easily exhausted and compromised as a result of the complex needs of the clinical trial system. The inventor has also identified that contextual diagnoses and tracking of physiological parameters and physical symptoms for cancer patients in remote or developing areas is not possible without the use of computing resources. As such, there exists a dire need for the present system.

The present system reduces the time to gather a statistically significant amount of data in a clinical trial because the patient data collected by the present system serves as a pre-admission qualifier to a clinical trial. A patient can be notified that he or she is qualified specifically for a clinical trial without the patient having to explore several clinical trial options and risk rejection.

The present system provides real time contextualization of contemporary symptom reporting with the context of treatment types, medications and previous illness/diseases or conditions. For example, the present system may let a doctor know that a patient's leg pain began three days after starting Lipitor®.

The present system provides real-time translation and conveyance of symptoms such that any language differences between a patient and doctor become irrelevant.

Definitions

As used herein, the terms "data," "content," "information," and similar terms may be used interchangeably to refer to data capable of being transmitted, received, and/or stored in accordance with embodiments of the present disclosure. Thus, use of any such terms should not be taken to limit the spirit and scope of embodiments of the present disclosure. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

The term "client device" refers to computer hardware and/or software that is configured to access a service made available by a server. The server is often (but not always) on another computer system, in which case the client device accesses the service by way of a network. Client devices may include, without limitation, smart phones, tablet computers, laptop computers, wearables, personal computers, enterprise computers, and the like.

The terms "user" or "patient" should be understood to refer to an individual, group of individuals, business, organization, and the like; the users referred to herein are accessing a predictive and interactive diagnostic system using client devices.

The term "physician" should be understood to refer to an individual, group of individuals, business, organization, and the like, serving in a physician-like capacity; the physicians referred to herein are accessing a predictive and interactive diagnostic system using client devices.

The terms "user profile," "client profile," "patient profile," "user account," and "user account details" refer to information associated with a user, including, for example, a user identifier, an email address, a real name (e.g., John Doe), a username (e.g., jdoe), a password, a real name, a time zone, a status, demographics, historical symptom data, medical history, current treatments and/or medications, and the like. The user account details can include a subset designation of user credentials, such as, for example, login information for the user including the user's username and password.

The term "network time" refers to timestamps defined by a computer, server, or communications network. A timestamp is a sequence of characters or encoded information identifying when a certain event occurred, usually giving date and time of day, sometimes accurate to a small fraction of a second. For example, a message containing symptom data may comprise a timestamp that indicates when it was created or last modified.

As used herein, the term "likelihood" refers to a measure of probability for occurrence of a particular event. For example, the likelihood that a symptom or set of symptoms may lead to a particular diagnosis may be a value associated with a specific scale. In some implementations, the machine predictions discussed above are based, at least in part, on the "likelihood" that an event will occur. Similarly, in some implementations, machine predictions are based on attributes associated with a client or patient profile and/or an associated symptom data.

The term "electronic correspondence" refers to any form of data transmission in which a device rendered object may be included. For example, an electronic correspondence including symptom data may be transmitted to a client device so that a patient or physician using the client device may interact with the symptom data and provide or learn about its significance. It will be appreciated that any form of data can be included in the electronic correspondence.

Example System Architecture

Methods, apparatuses, and computer program products of the present disclosure may be embodied by any of a variety of devices. For example, the method, apparatus, and computer program product of an example embodiment may be embodied by a networked device (e.g., an interactive diagnostic system, such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile devices, such as a portable digital assistant (PDA), mobile telephone, smartphone, laptop computer, tablet computer, wearable, or any combination of the aforementioned devices.

FIG. 1 illustrates an example computing system 100 within which embodiments of the present disclosure may operate. Users (i.e. patients) may access an interactive diagnostic system 102 via a communications network 112 using client devices 108A-108N. Physicians may access an interactive diagnostic system 102 via a communications network 112 using client devices 110A-110N. The client devices 108A-108N may be computing devices that are operated by a user that is to receive health tracking data or information. The client devices 110A-110N may be computing devices that are operated by medical doctors, researchers, or other users of interest. Moreover, the interactive diagnostic system 102 may comprise one or more servers 104 and one or more databases 106.

The server 104 may be embodied as a single computer or multiple computers. The server 104 may provide for receiving of electronic data from various sources, including but not necessarily limited to the user devices 108A-108N and the physician devices 110A-110N. For example, the server 104 may be operable to receive and process symptom data and graph data reports from the client devices 108A-108N indicative of physical health parameters of the users accessing the client devices. The graph data reports may be generated by the client devices 108A-108N such as based on monitoring symptom data provided to the client device defining symptoms and severities associated with the symptoms of a user. When the client devices 108A-108N are mobile devices (e.g., smartphone, wearable, etc.), the client devices 108A-108N may be carried on a user's person and facilitate the (e.g., real-time) recording of symptom data. As discussed in greater detail herein, the client devices 108A-108N may further generate graph data based on the symptom data, and generate the graph data report based on the graph data.

The server 104 may be further configured to receive the graph data reports from the user devices 108A-108N via the network 112 over time, and generate a (e.g., real-time), aggregated report based on the graph data reports received over time. The server 104 may be further configured to provide data analytics, such as by processing the reports to generate a user profile. The server 104 may further aggregate graph data reports of multiple users. User data may be combined, de-identified, and otherwise processed to create research data (e.g., in a format that can be inputted into standard research designs).

The server 104 may be further configured to provide notification services. For example, the reports may be used to determine a treatment, diminished health or a medical condition. In response, notifications can be sent to the client devices 108A-108N and/or physician devices 110A-110N. When a treatment is determined, a notification may be sent to the client devices 108A-108N via the network 112. In another example, a notification indicating a treatment, diminished health or medical condition may be sent to the physician devices 110A-110N via the network to facilitate user care. Although a single server 104 is shown, system 102 may include one or more servers 104. In some embodiments, the one or more servers 104 may include analytic circuitry 212, as shown in FIG. 2.

Returning to FIG. 1, database 106 may be embodied as a data storage device such as a Network Attached Storage (NAS) device or devices, or as a separate database server or servers. The database 106 includes information accessed and stored by the server 104 to facilitate the operations of the central system 102. For example, the database 106 may include, without symptom data (i.e., including associated time and location data, image data, etc., graph data, graph data reports, user input data, real-time or aggregated reports, research data, health status data, medical condition data, and/or the like.

The client devices 108A-108N may be any computing device as known in the art and operated by a user. The client devices 108A-108N may include mobile devices, such as laptop computers, smartphones, netbooks, tablet computers, wearable devices (e.g., electronic watches, wrist bands, glasses, etc.), and the like. Such mobile devices may provide their procured data to the server 104 and receive notifications and other informational displays that are relevant to the sent data. In some embodiments, the client devices 108A-108N may include wired or stationary devices such as desktop computers or workstations.

The physician devices 110A-110N may be any computing device as known in the art and operated by a physician, medical researcher, emergency responder, or other healthcare professional. The physician devices 110A-110N may include mobile devices, such as laptop computers, smartphones, netbooks, tablet computers, wearable devices (e.g., electronic watches, wrist bands, glasses, etc.), and the like. Such mobile devices may provide their procured data to the server 104 and receive notifications and other informational displays that are relevant to the sent data. In some embodiments, the physician devices 110A-110N may include wired or stationary devices such as desktop computers or workstations.

In embodiments where a client device 108A-108N and/or a physician device 110A-110N is a mobile device, such as a smart phone, wearable, or tablet, the client device 108A-108N and/or a physician device 110A-110N may execute an "app" or "application" to interact with the central system 102, such as a health tracking application. Apps are typically designed to execute on mobile devices. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications in a manner that allows for improved interactions between apps while also preserving the privacy and security of consumers. In some embodiments, a mobile operating system may also provide for improved communication interfaces for interacting with external devices (e.g., home automation systems, indoor navigation systems, and the like). Communication with hardware and software modules executing outside of the app is typically provided via application programming interfaces (APIs) provided by the mobile device operating system.

Additionally or alternatively, the client devices 108A-108N and physician devices 110A-110N may interact with the interactive diagnostic system 102 via a web browser. As yet another example, the client devices 108A-108N and physician devices 110A-110N may include various hardware or firmware designed to interface with the interactive diagnostic system 102 (e.g., where the client device 108A-

108N is a purpose-built device offered for the primary purpose of communicating with the central system 102, such as a medical monitoring device).

Communications network 112 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 104 may include a cellular telephone, an 802.11, 802.16, 802.20, and/or WiMax network. Further, the communications network 104 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the group-based communication system. In some embodiments, the protocol is a custom protocol of JSON objects sent via a Websocket channel. In some embodiments, the protocol is JSON over RPC, JSON over REST/HTTP, and the like.

Example Apparatus for Implementing Embodiments of the Present Disclosure

The server 104, database 106, client device 108A-108N or physician device 110A-110N may be embodied by one or more computing systems or devices, such as apparatus 200 shown in FIG. 2. As illustrated in FIG. 2, the apparatus 200 may include a processor 202, a memory 204, an input/output circuitry 206, communications circuitry 208, a health tracking circuitry 210, and analytics circuitry 212. The apparatus 200 may be configured to execute the operations described herein. Although these components 202-212 are described with respect to functional limitations, it should be understood that the particular implementations necessarily include the use of particular hardware. It should also be understood that certain of these components 202-212 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the apparatus 200 may provide or supplement the functionality of particular circuitry. For example, the processor 202 may provide processing functionality, the memory 204 may provide storage functionality, the communications circuitry 208 may provide network interface functionality, and the like.

In some embodiments, the processor 202 (and/or co-processor or any other processing circuitry assisting or otherwise associated with the processor) may be in communication with the memory 204 via a bus for passing information among components of the apparatus 200. The memory 204 may be non-transitory and may include, for example, one or more volatile and/or non-volatile memories. In other words, for example, the memory may be an electronic storage device (e.g., a computer readable storage medium). The memory 204 may be configured to store information, data, content, applications, instructions, or the like, for enabling the apparatus to carry out various functions in accordance with example embodiments of the present disclosure.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 204 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, the apparatus 200 may include input/output circuitry 206 that may, in turn, be in communication with processor 202 to provide output to the user and, in some embodiments, to receive an indication of a user input. The input/output circuitry 206 may comprise a user interface and may include a display and may comprise a web user interface, a mobile application, a client device, a kiosk, or the like. The input/output circuitry 206 may include a camera and touch screen. In some embodiments, the input/output circuitry 206 may also include medical sensors, keyboard, a mouse, a joystick, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the apparatus 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

When circuitry 200 is implemented on a server 104, circuitry 200 may include analytics circuitry 212. The analytics circuitry 212 may include hardware configured to generate reports based on information received from user devices 108, provide analytics, and notifications.

When circuitry 200 is implemented on a client device 108A-108N, the circuitry 200 may include health tracking circuitry 210. The health tracking circuitry 210 may include hardware configured to monitor symptom data and other user inputs, generate graph data and graph data reports for the interactive diagnostic system 102, and interface with the central system 102 as discussed herein.

Circuitries 210 and 212 may utilize processing circuitry, such as the processor 202, to perform these functionalities. However, it should also be appreciated that, in some embodiments, circuitries 210 and 212 may include a separate processor, specially configured field programmable gate array (FPGA), or application specific interface circuit (ASIC). Circuitries 210 and 212 may therefore be implemented using hardware components of the apparatus configured by either hardware or software for implementing these planned functions.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example displays discussed herein can be based on data that is received, generated and/or maintained by one or more components of apparatus 200. In some embodiments, one or more external systems (such as a remote cloud computing and/or data storage system) may also be leveraged to provide at least some of the functionality discussed herein.

As described above and as will be appreciated based on this disclosure, embodiments of the present disclosure may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Processed for Predictive and Interactive Diagnoses and Tracking

FIG. 3 shows a flow chart of an example of a method 300 for health tracking with a mobile user device (or "mobile device"), in accordance with some embodiments. Method 400 is discussed with respect to cancer health tracking, but similar techniques may be alternatively or additionally applied to tracking of other medical conditions.

Method 300 may begin at 302 and proceed to 304, where processing circuitry of a mobile device (e.g., client device 108A-108N) may be configured to receive symptom data via a user interface of the mobile device over time. The symptom data may define one or more symptoms (e.g., physical or mental conditions, side effects of a treatment, etc.) and severities associated with the one or more systems. The mobile device may be configured to execute a health tracking application. The health tracking application may provide for the user interface, which may be displayed on a display of the mobile device.

The user interface may be configured to provide displays and to operate with an input device of the mobile device, such as a touch screen. FIGS. 7-11 illustrate exemplary user interfaces for use with embodiments of the present disclosure. FIG. 9, for example, shows an example of a user interface 900, in accordance with some embodiments. The user interface 900 may include an application menu 902 and an application page region 904. The application menu 902 may provide for user navigation through the various functionalities of the mobile device as discussed herein, and thus may include a record button 906, a report button 908, a journal button 910, and a settings button 912. Each of the buttons 906-912 may be selected, such as via touch screen, and in response, a suitable user interface may be provided to the application page 904. For example, the record button 906 may provide a reference to a symptom data input user interface 914 configured to allow entry of the symptom data. The report button 908 may provide a reference to a report interface configured to provide graph data reports, graphs, etc. programmatically generated based on the symptom data. The journal button 910 may provide a reference to a journal interface where the user can provide notes, concerns, feelings, etc. as user input. The settings button 912 may provide for application settings (e.g., notification settings, data sharing settings, account/profile settings, user, interface settings, etc.).

In response to selection of the record button 906, a symptom data input interface 914 may be provided to the application page 904. The symptom data input interface 914 may include indications of one or more symptoms, and allow the user to specify a severity associated with each symptom (e.g., ranging from none, mild, moderate, severe, and very severe). The mobile device may be configured to select the symptoms within the symptom data input interface 914, such as based on the health condition being monitored. In the example of cancer monitoring, some example symptoms may include bone pain, fatigue, fever, hot flashes, scary thoughts, etc. The symptoms may be programmatically generated, or may be entered by the user.

The user may access the symptom data input interface 914 to enter symptom data at any suitable time. Because the mobile device can be carried by the user, the user can advantageously enter the symptom data as a symptom is being experienced or directly thereafter. As discussed above, conventional self-reporting techniques used by physicians (e.g., during a patient live examination) rely on patient recall of past symptoms or side effects, and thus may be less accurate and reliable. When the user has entered the symptom data, the symptom data may be saved (e.g., in a memory) or otherwise stored for future use (e.g., in a database), such as in response to the user selecting the record symptom data button 916 within the symptom data input interface 914.

In some embodiments, the symptom data may include image data. For example, the user may capture image data with a camera of the mobile device based on selecting image capture button 918. In response, an image capture interface may be provided that allows the user to capture images of symptoms for a visual reporting. Symptoms such as rash, bleeding suture, discoloration of the body or body excretion, etc. may be particularly useful to report in a visual format. As discussed above, users may have difficulty recalling symptoms. For visual symptoms that are subject to change over time), the mobile device may provide for real-time capture of image data in connection with recordation of the symptom data by the user.

In some embodiments, the symptom data may include other types of user input data provided via the user interface such as journal data, user concerns, user demographics, user medical history, user medications, or user treatment types. For example, the user may provide journal data to the mobile device based on selecting the journal button 910. In response to the selection, the mobile device may be configured to provide journal interface where the user can provide notes, concerns, feelings, etc. as user input. The mobile device may be further configured to associate the user input data with the symptom data and/or other information derived from the symptom data such as graph data or the graph data report as discussed in greater detail below.

In some embodiments, the symptom data may be generated by sensors of the mobile device to track user symptoms. Such medical sensors may be configured to track user physiological characteristics, such as heart rate, blood oxygen, skin temperature, body fat, skeletal mass, sweat, etc. Thus the mobile device may include a heart rate or blood flow sensor, an oximetry sensor, a skin conductance sensor, a skin temperature sensor, etc. When the mobile device is a wearable device (e.g., a smartwatch), such sensors can provide continuous health tracking and symptom data capture when worn by the user. In some embodiments, the mobile device may be configured to provide a step graph user interface for entry of the symptoms and associated severities over time.

At 306, the mobile device may be configured to determine time data associated with the symptom data. The time data may indicate a date and time of day associated with the symptom data provided by the user. The mobile device may be configured to provide a clock and/or calendar to record the time data automatically when symptom data is captured. In another example, the user may be allowed to specify the time data for entered symptom data. As such, the mobile device is able to determine the user's symptoms, the severity of the symptoms, and the times (e.g., including durations, regularity of occurrence, etc.) of the symptoms/severities.

At 308, the mobile device may be configured to determine location data associated with the symptom data. The location data may be determined using any suitable technique. For example, the mobile device may be configured to integrate with mobile device location services, utilize global positioning systems (GPS), cell-tower triangulation, personal area networks (e.g., Bluetooth, WiFi, etc.), etc. to programmatically determine the location. The capture of location data may be performed in connection with the receiving of symptom data such that the locations where the user experienced each symptom may also be tracked. In another example, the user may manually enter the location data.

At 310, the mobile device may be configured to generate graph data based on the symptom data and the time data. The graph data may provide an effective presentation of the symptom data. The graph data may be determined based on the user inputs provided by the user, such as based on the symptom data, time data, location data, etc. In some embodiments, the graph data may include a step graph for each symptom where severity of the symptom is plotted against the time data. Thus the step graph provides a graphical and easy to understand format for organizing the symptom data. In some embodiments, the location data may be further associated with the graph data. For example, each bar of the step graph may provide a reference or other indication of the associated location data The graph data may be viewed within the user interface of the mobile device. In some embodiments, the mobile device may be configured to provide the graph data as an output. For example, the graph data may be output as a text file of comma-separated values (CVS), as a Portable Document Format (pdf) file, image file, document file, etc. The output file may be shared with the central system 102 or a physician device 110, or any other device as specified by the user.

At 312, the mobile device may be configured to provide the graph data to the one or more servers 104 via the network 112. The graph data, and the other data captured by the mobile device, may be stored in a memory of the mobile device. The memory may be accessed when appropriate to transmit the graph data to the server 104 of the central system 102.

At 314, the one or more servers 104 (e.g., processing circuitry of a server 104 of the central system 102) may be configured be configured to generate a graph data report based on the graph data. The graph data report may include a collection of graph data collected within a period of time (e.g., a day, a week, a month, etc.), as well as the other types of associated data captured by the mobile device (e.g., location data, journal data, etc.). For example, journal data entered by user input may be attached to the graph data report. The graph data report may be generated based on user request, such as in response to the user selecting the report button 408 within the application menu 402 of the user interface 400. Furthermore, the generated graph data report may be provided to the user interface in response to selection of the report button 408.

At 316, the one or more servers may be configured to receive the graph data over time from the mobile device via the network and generate/update the graph data report. In some embodiments, the mobile device may be configured to facilitate improved connectivity. For example, mobile applications often require active network connections (e.g., Internet) to a server in order to achieve interaction with remote services for desired functionality. Such applications are not operable when the active network connection is not available. To provide improved connectivity and reliable symptom recordation on the mobile device, the mobile device may be configured to store the graph data report (including symptom data, and graph data) within a memory, and poll the server 104 for connectivity (e.g., intermittently, on a scheduled basis, in response to a user request, in response to a request from the sever 104, etc.). The mobile device may be further configured to provide one or more of the symptom data or the graph data to the server 104 via the network 112 when the connection to the server 104 via the network 112 is available. The system 102 may be configured to store the data received from the mobile device for subsequent analysis, such as within the database 106.

At 318, the one or more servers may be configured to generate/update a user profile based on the graph data reports over time. The user profile may provide for an organized collection of data associated with the user. The associated data may include symptom data, time data, location data, graph data, graph data reports, etc. such that each piece of user information is stored at the "backend" of system 102 (e.g., within a database 106). In some embodiments, the user profile may be generated based on the user creating an account with the central system, and may be updated over time based on the graph data reports received from the mobile device over time.

At 320, the one or more servers may be configured to generate an aggregated report based on the graph data reports over time. The aggregated report may provide for a programmatic analysis of the user's health status, medication and treatment impact of symptoms, side effects, quality of life, etc.

At 322, the one or more servers may be configured to determine a treatment based on the user profile, graph data reports over time, or the aggregated report. The treatments may be associated with health conditions, symptoms, or side effects, and the one or more servers may be configured to match the user's data with a suitable treatment. In some embodiments, an algorithmic scoring may be used to select users that are suitable or optimal for a particular treatment or clinical trial, and the top ranking users based on the scoring may be selected for a particular treatment or clinical trial. In some embodiments, the server may communicate with physician devices via the network to receive notifications regarding treatments, clinical trials, etc., which may then be matched to users based on information received from their mobile devices.

At 324, the one or more servers may be configured to send the graph data report or a notification of the treatment to the user device via the network. The notification may be provided to the user interface of the mobile device. The notification may indicate that the user should participate in a treatment or clinical trial, is eligible for the treatment, or may indicate steps or other guidance in connection with administration of the treatment. Advantageously, the aggregation of graph data reports over time provides for large volumes of user data that allow for more accurate diagnosis and treatment selection for the user by the central system. Advantageously, the mobile device may be notified regarding relevant and sometimes rare treatment opportunities that might otherwise go overlooked or be unknown to the patient's doctors.

In some embodiments, the mobile device may be configured to generate the graph data report, or perform some of the other graph data processing functionality discussed herein with respect to the one or more servers, such as updating user profiles, generating graph data reports or aggregated reports, determining treatments, sending notifications, etc.

At 326, the one or more servers may be configured to provide a notification to a physician device via the network. The notification to the physician device may be provided when programmatic analysis of the graph data reports indicates that the user may have a diminished health or a medical condition. For example, if the user inputs nausea multiple times for the symptom data, the mobile device may be configured to send the notification to a physician that the user is at risk of dehydration. If that same user had inputted a Gastrointestinal cancer, the notification may prompt the physician to contact the user for additional or increased treatment. In some embodiments, the physician device may be selected from multiple physician devices based on the location data. For example, physicians may be scored and ranked based on proximity to the user, and the physician device may be selected accordingly to perform location-based matching of patients and physicians. As such, the speed and reliability of physician or emergency contact notification is improved by leveraging the central system as a networked intermediary for remote communications between user mobile devices and physician devices. In some embodiments, the one or more servers and/or physician device may be configured to provide a dashboard or user interface for the physician device configured to receive notifications. The notifications may include alerts regarding a patient, such as (changes) deterioration or improvement in health that the physician may set as a warning level for changing treatment or starting emergency treatment. The dashboard may also include a research tool that can display data from either one patient at a time, a collection of patients with particular criteria, or all patients.

At 328, the one or more servers may be configured to aggregate graph data reports of multiple users to generate research data. The research data may include algorithmic transformations of the symptom data, time data, graph data, etc. such that the information regarding the user's health status is in a format that is compatible with standard research specifications. The user data may be de-identified and sorted in the course of the aggregation to provide improved big data processing without compromising patient confidentiality. In some embodiments, the information may be formatted into training sets configured to facilitate supervised or semi-supervised machine learning. For example, training sets including symptom data (e.g., the inputs) and associated conditions or treatments (e.g., the outputs) may be generated, and used to train a machine learning algorithm (e.g., regression algorithms, instance-based algorithms, regularization algorithms, decision tree algorithms, neural network algorithms, etc.) that programmatically discovers relationships between the inputs and the outputs. The trained machine learning algorithm may then be used to facilitate various functionalities discussed herein, such as diagnosing or matching a treatment to the user.

At 330, the one or more servers may be configured to provide the research data to a physician device via the network. Method 300 may then proceed to 332 and end.

FIG. 4 is an exemplary predictive and interactive diagnostic data flow according to one embodiment of the present disclosure. New system data that has been submitted via a user interface is received 401. Metadata associated with the symptom data is extracted 402. Historical symptom data is retrieved 403, and the combined new symptom data and historical symptom data, in addition to their associated metadata, are utilized to generate a graph and/or report 404. The graph and/or report can be transmitted 405 to a requesting device. Optionally, a predicted value can be generated 406 based on the new and historical symptom data, as well as other sources of data. The predicted value can trigger 407 some sort of action. The triggered action can be, for example, a notification transmitted to a computing device a hospital dispatcher, medical professional, family member, and the like. The triggered action can also be, for example, a notification transmitted to and displayed on the client device alerting them to a particular condition that is possible as a result of the predicted value.

FIG. 5 is an exemplary predictive and interactive diagnostic data flow according to one embodiment of the present disclosure. A request is received from a client device 501. Historical symptom data and historical predicted values are retrieved 501. Recommendations are generated 503 based upon the historical symptom data and predicted values. The recommendations can be transmitted for display 504 to the requesting device. Recommendations can be, for example, adjustments in treatment, questions to ask a medical professional immediate, questions to ask a medical professional upon a subsequent meeting with the medical professional, and the like.

FIG. 6 is an exemplary predictive and interactive diagnostic data flow according to one embodiment of the present disclosure. A request is received from a client device 601, and a request is transmitted along with patient data to a physician device 602. Recommendations are also generated based upon the historical patient data and predicted values associated with the patient 603, and the recommendations are transmitted for display 604 at the physician device. A selection of and of the recommendations is received from the physician device 605. The selected recommendations are transmitted for display 606 at the requesting client device.

Many modifications and other embodiments will come to mind to one skilled in the art to which these embodiments pertain having the benefit of the teachings presented in the foregoing descriptions and the associated drawings. Therefore, it is to be understood that embodiments and implementations are not to be limited to the specific example embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus comprising at least one processor and at least one memory for storing instructions that, with the at least one processor, cause the apparatus to:
   receive, via a network and from a patient mobile device associated with a user, cancer symptom data via interactions with a user interface of the patient mobile device, the cancer symptom data comprising a plurality of cancer symptom severity data points, each cancer symptom severity data point associated with a unique timestamp, one or more cancer symptoms, and one or more severities associated with the one or more cancer symptoms for the user, wherein each unique timestamp associated with each cancer symptom severity data point is generated by the patient mobile device at a time at which the user reported in real-time the one or more cancer symptoms, and wherein the cancer symptom data further comprises real-time capture of image data;
   generate an aggregated report associated with the user based upon a time course of cancer symptom severity experienced by the user based on the plurality of cancer symptom severity data points and the unique timestamp associated with each cancer symptom severity data point;
   generate research data by aggregating a plurality of aggregated reports associated with a plurality of users;
   train, using the research data, one or more predictive machine learning models comprising a regression algorithm, an instance-based algorithm, a regularization algorithm, a decision tree algorithm, or a neural network algorithm;
   generate, using the one or more predictive machine learning models, a predicted value associated with a cancer condition based at least in part on the aggregated report associated with the user, wherein the predicted value comprises a likelihood that the user has the cancer condition;
   compare the predicted value to a warning level associated with a physician device; and
   in response to determining that the predicted value exceeds the warning level;
   generate, based at least in part on the predicted value one or more user questions, each user question associated with an urgency level, wherein the urgency level indicates how soon the user should ask a medical professional the user question;
   transmit the aggregated report, the real-time capture of image data, and the predicted value associated with the cancer condition to the physician device such that the aggregated report, the real-time capture of image data, and the predicted value associated with the cancer condition are configured to be displayed on the physician device; and
   transmit the predicted value and the one or more user questions to the patient mobile device, wherein the predicted value and the one or more user questions are configured to be displayed on the patient mobile device.

2. The apparatus of claim 1, wherein the at least one memory for storing instructions, with the at least one processor, further cause the apparatus to:
   rank a plurality of physician devices based at least in part on location data determined using global positioning systems (GPS) circuitry of the patient mobile device.

3. The apparatus of claim 1, wherein the at least one memory for storing instructions, with the at least one processor, further cause the apparatus to:
   associate location data with each cancer symptom severity data point, wherein the location data is determined using GPS circuitry of the patient mobile device and is received via the network from the patient mobile device.

4. The apparatus of claim 1, wherein the at least one memory for storing instructions, with the at least one processor, further cause the apparatus to:
   receive graph data, via the network and from the patient mobile device, wherein the graph data comprises the time course of cancer symptom severity experienced by the user based on the plurality of cancer symptom severity data points and the unique timestamp associated with each cancer symptom severity data point.

5. The apparatus of claim 4, wherein the at least one memory for storing instructions, with the at least one processor, further cause the apparatus to:
   generate a graph data report based on the graph data, wherein the aggregated report associated with the user is based upon the graph data report.

6. The apparatus of claim 5, wherein the at least one memory for storing instructions, with the at least one processor, further cause the apparatus to:
   responsive to receiving one or more subsequent cancer symptom severity data points associated with the user and generating a subsequent graph data report based on the graph data report and the one or more subsequent cancer symptom severity data points, automatically update the aggregated report to include the subsequent graph data report.

7. The apparatus of claim 1, wherein the at least one memory for storing instructions, with the at least one processor, further cause the apparatus to:
   in accordance with the predicted value satisfying a trigger and upon determining, based at least in part on the aggregated report and independent from a request from the patient mobile device associated with the user, that the user is eligible for a given clinical trial, generate a notification configured for rendering via a user interface of the patient mobile device, the notification comprising at least one of: data representing eligibility of the user for the given clinical trial or data providing information about the given clinical trial.

8. The apparatus of claim 7, wherein the at least one memory for storing instructions, with the at least one processor, further cause the apparatus to:
   transmit the notification and the aggregated report to the patient mobile device, wherein the aggregated report is configured to serve as a pre-admission qualifier in an admission process of the user for the given clinical trial.

9. The apparatus of claim 2, wherein the at least one memory for storing instructions, with the at least one processor, further cause the apparatus to:
transmit the aggregated report and the predicted value associated with the cancer condition to a physician device of the plurality of physician devices that is selected according to the ranking.

10. A computer program product comprising at least one non-transitory computer-readable storage medium having computer-readable program code portions stored therein, the computer-readable program code portions configured to:
receive, via a network and from a patient mobile device associated with a user, cancer symptom data via interactions with a user interface of the patient mobile device, the cancer symptom data comprising a plurality of cancer symptom severity data points, each cancer symptom severity data point associated with a unique timestamp, one or more cancer symptoms, and one or more severities associated with the one or more cancer symptoms for the user, wherein each unique timestamp associated with each cancer symptom severity data point is generated by the patient mobile device at a time at which the user reported in real-time the one or more cancer symptoms, and wherein the cancer symptom data further comprises real-time capture of image data;
generate an aggregated report associated with the user based upon a time course of cancer symptom severity experienced by the user based on the plurality of cancer symptom severity data points and the unique timestamp associated with each cancer symptom severity data point;
generate research data by aggregating a plurality of aggregated reports associated with a plurality of users;
train, using the research data, one or more predictive machine learning models comprising a regression algorithm, an instance-based algorithm, a regularization algorithm, a decision tree algorithm, or a neural network algorithm;
generate, using the one or more predictive machine learning models, a predicted value associated with a cancer condition based at least in part on the aggregated report associated with the user, wherein the predicted value comprises a likelihood that the user has the cancer condition;
compare the predicted value to a warning level associated with a physician device; and
in response to determining that the predicted value exceeds the warning level;
generate, based at least on the predicted value, one or more user questions, each user question associated with an urgency level, wherein the urgency level indicates how soon the user should ask a medical professional the user question;
transmit the aggregated report, the real-time capture of image data, and the predicted value associated with the cancer condition to the physician device such that the aggregated report, the real-time capture of image data, and the predicted value associated with the cancer condition are configured to be displayed on the physician device; and
transmit the predicted value and the one or more user questions to the patient mobile device, wherein the predicted value and the one or more user questions are configured to be displayed on the patient mobile device.

11. The computer program product of claim 10, wherein the computer-readable program code portions are further configured to:
rank a plurality of physician devices based at least in part on location data determined using global positioning systems (GPS) circuitry of the patient mobile device.

12. The computer program product of claim 10, wherein the computer-readable program code portions are further configured to:
associate location data with each cancer symptom severity data point, wherein the location data is determined using GPS circuitry of the patient mobile device and is received via the network from the patient mobile device.

13. The computer program product of claim 10, wherein the computer-readable program code portions are further configured to:
receive graph data, via the network and from the patient mobile device, wherein the graph data comprises the time course of cancer symptom severity experienced by the user based on the plurality of cancer symptom severity data points and the unique timestamp associated with each cancer symptom severity data point.

14. The computer program product of claim 13, wherein the computer-readable program code portions are further configured to:
generate a graph data report based on the graph data, wherein the aggregated report associated with the user is based upon the graph data report.

15. The computer program product of claim 14, wherein the computer-readable program code portions are further configured to:
responsive to receiving one or more subsequent cancer symptom severity data points associated with the user and generating a subsequent graph data report based on the graph data report and the one or more subsequent cancer symptom severity data points, automatically update the aggregated report to include the subsequent graph data report.

16. A computer-implemented method, comprising:
receiving, using a processor via a network and from a patient mobile device associated with a user, cancer symptom data entered via interactions with a user interface of the patient mobile device, the cancer symptom data comprising a plurality of cancer symptom severity data points, each cancer symptom severity data point associated with a unique timestamp, one or more cancer symptoms for the user, and one or more severities associated with the one or more cancer symptoms for the user, wherein each unique timestamp associated with each cancer symptom severity data point is generated by the patient mobile device at a time at which the user reported in real time the one or more cancer symptoms, and wherein the cancer symptom data further comprises real-time capture of image data;
generating, using the processor, an aggregated report associated with the user based upon a time course of cancer symptom severity experienced by the user based on the plurality of cancer symptom severity data points and the unique timestamp associated with each cancer symptom severity data point;
generating research data by aggregating a plurality of aggregated reports associated with a plurality of users;
training, using the research data, one or more predictive machine learning models comprising a regression algorithm, an instance-based algorithm, a regularization algorithm, a decision tree algorithm, or a neural network algorithm;

generating, using the one or more predictive machine learning models, a predicted value associated with a cancer condition based at least in part on the aggregated report associated with the user, wherein the predicted value comprises a likelihood that the user has the cancer condition;

compare the predicted value to a warning level associated with a physician device; and in response to determining that the predicted value exceeds the warning level;

generate, based at least in part on the predicted value, one or more user questions, each user question associated with an urgency level, wherein the urgency level indicates how soon the user should ask a medical professional the user question;

transmit the aggregated report, the real-time capture of image data, and the predicted value associated with the cancer condition to the physician device such that the aggregated report, the real-time capture of image data, and the predicted value associated with the cancer condition are configured to be displayed on the physician device; and transmit the predicted value and the one or more user questions to the patient mobile device, wherein the predicted value and the one or more user questions are configured to be displayed on the patient mobile device.

17. The apparatus of claim 1, wherein the one or more user questions comprise at least one of (i) a high urgency question to immediately ask a medical professional and (ii) a moderate urgency question to ask the medical professional in a subsequent meeting.

18. The apparatus of claim 17, wherein an indication of a urgency level of each question of the one or more user questions is configured to be displayed on the patient mobile device.

19. The apparatus of claim 1, wherein the apparatus is further configured to:

generate, based at least in part on the predicted value, one or more physician recommendations; and transmit the one or more physician recommendations to the physician device, wherein the one or more physician recommendations are configured to be displayed on the physician device.

20. The apparatus of claim 19, wherein the apparatus is further configured to:

receive, via the physician device, a selection of at least one recommendation of the one or more physician recommendations; and transmit the at least one recommendation of the one or more physician recommendations to the patient mobile device, wherein the at least one recommendation of the one or more physician recommendations is configured to be displayed on the patient mobile device.

* * * * *

UNITED STATES PATENT AND TRADEMARK OFFICE
CERTIFICATE OF CORRECTION

| | | |
|---|---|---|
| PATENT NO. | : 12,165,769 B2 | Page 1 of 1 |
| APPLICATION NO. | : 17/887818 | |
| DATED | : December 10, 2024 | |
| INVENTOR(S) | : Darryl Mitteldorf | |

It is certified that error appears in the above-identified patent and that said Letters Patent is hereby corrected as shown below:

In the Claims

<u>Column 15,</u>
Line 60, "value one" should read --value, one--.

<u>Column 17,</u>
Line 51, "at least" should read --at least in part--.

Signed and Sealed this
Twelfth Day of August, 2025

Coke Morgan Stewart
*Acting Director of the United States Patent and Trademark Office*